United States Patent
Abe et al.

(10) Patent No.: US 8,523,819 B2
(45) Date of Patent: *Sep. 3, 2013

(54) INTERNAL NEEDLE

(75) Inventors: Kazuhiro Abe, Fukuroi (JP); Yoshihiro Wada, Fukuroi (JP); Shigeaki Funamura, Fukuroi (JP)

(73) Assignee: Covidien LP, Mansfield, MA (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/279,580

(22) Filed: Oct. 24, 2011

(65) Prior Publication Data

US 2012/0123339 A1  May 17, 2012

Related U.S. Application Data

(62) Division of application No. 12/095,261, filed as application No. PCT/JP2006/324128 on Nov. 27, 2006, now Pat. No. 8,043,265.

(30) Foreign Application Priority Data

Nov. 28, 2005 (JP) ................................ 2005-341866

(51) Int. Cl.
*A61B 17/34* (2006.01)
(52) U.S. Cl.
USPC ................ 604/164.08; 604/192; 604/263
(58) Field of Classification Search
USPC ..... 604/110, 164.01, 164.08, 164.11–164.12, 604/192, 198, 263
See application file for complete search history.

(56) References Cited

U.S. PATENT DOCUMENTS

| | | | |
|---|---|---|---|
| 4,834,718 A | 5/1989 | McDonald | |
| 4,929,241 A | 5/1990 | Kulli | |
| 4,952,207 A | 8/1990 | Lemieux | |
| 4,964,854 A | 10/1990 | Luther | |
| 5,049,136 A | 9/1991 | Johnson | |
| 5,053,017 A | 10/1991 | Chamuel | |
| 5,135,504 A | 8/1992 | McLees | |
| 5,183,468 A | 2/1993 | McLees | |
| 5,300,045 A | 4/1994 | Plassche, Jr. | |
| 5,328,482 A | 7/1994 | Sircom et al. | |
| 5,344,408 A | 9/1994 | Partika | |
| 5,419,766 A * | 5/1995 | Chang et al. | 604/110 |
| 5,558,651 A * | 9/1996 | Crawford et al. | 604/263 |

(Continued)

FOREIGN PATENT DOCUMENTS

| | | |
|---|---|---|
| JP | 2002285558 | 11/1990 |
| JP | 2002248168 | 9/2002 |
| JP | 2004073403 | 3/2004 |

OTHER PUBLICATIONS

Notification of Reasons for Refusal for corresponding Japanese application 2005-341866, mailed Jun. 1, 2011 (in Japanese).

*Primary Examiner* — Quynh-Nhu H Vu
(74) *Attorney, Agent, or Firm* — Lisa E. Winsor, Esq.

(57) ABSTRACT

An indwelling needle is provided which has a simple structure and is capable of securely mounting a needle tip protective tool on the tip portion of an internal needle. The indwelling needle A includes an external needle including a cannula and a housing, an internal needle including a metal needle and a hub and a needle tip protective tool. The needle tip protective tool is mounted on the housing with the metal needle inserted into an inner section so that the metal needle can be removed together with the internal needle from the external needle.

10 Claims, 20 Drawing Sheets

(56) References Cited

U.S. PATENT DOCUMENTS

| | | |
|---|---|---|
| 5,599,310 A | 2/1997 | Bogert |
| 5,879,337 A | 3/1999 | Kuracina et al. |
| 6,117,108 A | 9/2000 | Woehr et al. |
| 6,203,527 B1 | 3/2001 | Zadini et al. |
| 6,221,047 B1 | 4/2001 | Greene et al. |
| 6,443,929 B1 | 9/2002 | Kuracina et al. |
| 6,585,704 B2 | 7/2003 | Luther et al. |
| 6,595,954 B1 * | 7/2003 | Luther et al. .......... 604/110 |
| 6,749,588 B1 | 6/2004 | Howell et al. |
| 7,112,191 B2 | 9/2006 | Daga |
| 7,160,269 B2 | 1/2007 | Woehr |
| 7,179,244 B2 | 2/2007 | Smith et al. |
| 7,186,239 B2 | 3/2007 | Woehr |
| 7,214,211 B2 | 5/2007 | Woehr et al. |
| 7,374,554 B2 | 5/2008 | Menzi et al. |
| 7,500,965 B2 | 3/2009 | Menzi et al. |
| 7,513,888 B2 | 4/2009 | Sircom et al. |
| 7,530,965 B2 | 5/2009 | Villa et al. |
| 7,534,227 B2 | 5/2009 | Kulli |
| 7,597,681 B2 | 10/2009 | Sutton et al. |
| 7,608,057 B2 | 10/2009 | Woehr et al. |
| 7,611,485 B2 | 11/2009 | Ferguson |
| 7,611,499 B2 | 11/2009 | Woehr et al. |
| 7,618,395 B2 | 11/2009 | Ferguson |
| 7,625,360 B2 | 12/2009 | Woehr et al. |
| 7,632,243 B2 | 12/2009 | Bialecki et al. |
| 7,651,476 B2 | 1/2010 | Kohler |
| 7,654,988 B2 | 2/2010 | Moulton et al. |
| 7,682,339 B2 | 3/2010 | Fujii |
| 8,043,265 B2 * | 10/2011 | Abe et al. .......... 604/164.08 |

* cited by examiner

US 8,523,819 B2

INTERNAL NEEDLE

CROSS REFERENCE TO RELATED PATENT APPLICATIONS

This application is a divisional application under 35 U.S.C. §121 and claims the benefit of U.S. patent application Ser. No. 12/095,261 filed Jul. 15, 2009, now U.S. Pat. No. 8,043,265, which is a U.S. National application of PCT/JP2006/324128 filed on Nov. 27, 2006, which claims the benefit of and priority to Japanese Patent Application No. 2005-341866 filed on Nov. 28, 2005; the contents of each of the above-identified applications is incorporated herein by reference in its entirety.

BACKGROUND OF THE INVENTION

1. Technical Field

The present disclosure pertains to a type of indwelling needle that is used in transfusion and blood collection for piercing and indwelling in a blood vessel of a patient.

2. Background of Related Art

In the prior art, indwelling needles have been used in various applications, such as hemodialysis or feeding of prescribed medicine solutions, etc. The indwelling needle includes an external needle having a needle tip for indwelling in a blood vessel of a patient and an internal needle that is inserted into the external needle to facilitate smooth piercing of the blood vessel of the patient. In operation, the internal needle is inserted into the external needle such that the tip portion of the internal needle protrudes from the tip portion of the external needle. Thereafter, together with the internal needle, the external needle pierces the blood vessel. Then, while the external needle indwells in the blood vessel, the internal needle is pulled out of the external needle (blood vessel), and a tube member or the like for feeding prescribed blood or medicine solution or the like is connected to the rear end portion of the external needle, and hemodialysis or feeding of a medicine solution or the like is carried out.

In the indwelling needle, there is a needle tip protective part for preventing the patient from being harmed by the needle tip of the internal needle which is pulled out of the external needle. The needle tip protective part has a tapered cylindrical body with an inner diameter larger on one end and smaller on the other end. The tip portion of the internal needle protected by the needle tip protective part is formed of a size that permits it to be inserted into the opening on one end of the needle tip protective part but not into the opening on the other end. Consequently, when the internal needle is pulled through the needle tip protective part, the tip end of the internal needle cannot pass through the opening on the other end of the needle tip protective part. Thus, the needle tip protective part is coupled to the tip portion of the internal needle and the tip portion of the internal needle is covered.

However, the aforementioned needle tip protective part of the prior art is prone to shifting position to the rear side of the internal needle. Consequently, the tip portion of the internal needle may be exposed. People have proposed a type of indwelling needle having a needle tip protective part that makes use of a spring member or the like to fix the protective part at the tip portion of the internal needle so that the tip portion of the internal needle can be reliably covered. However, for the indwelling needle, the number of parts increases, the manufacturing cost rises, and the resistance when the internal needle is pulled out of the external needle becomes higher, leading to poor operability. This is undesirable.

The purpose of the present disclosure is to solve the aforementioned problems of the prior art by providing a type of indwelling needle that has a simple structure, good operability, and can have the needle tip protective part mounted reliably on the tip portion of the internal needle.

SUMMARY

An indwelling needle is provided which includes an outer cannula for indwelling placement in a patient. The cannula has a housing attached to a proximal end thereof. An inner needle has a connection part at a proximal end thereof. A needle tip protector is positioned within the housing and around the inner needle. The needle tip protector comprises a first portion having a sidewall defining a through-hole of a first diameter and a second portion having a sidewall defining a through-hole of a second diameter, which is smaller than the first diameter. The sidewall of the first portion comprises at least one inwardly movable blocking member attached thereto. The inner needle has a tip portion and a main portion. The tip portion has a larger diameter than the main portion. The tip portion, the main portion and the second portions are dimensioned such that the main portion but not the tip portion is slidable through the through-hole of the second portion. The indwelling needle is configured such that withdrawing the inner needle from the cannula in a proximal direction causes the tip portion to engage with the second portion, thereby withdrawing the needle tip protector from the housing and causing the at least one blocking member to move inwardly into the first portion through-hole so as to trap the tip portion therein.

In one embodiment the needle tip protector comprises at least two blocking members which can be diametrically opposed to one another. The housing and the blocking members can be shaped such that on withdrawing the inner needle, the housing is arranged to exert inward pressure on the blocking members to cause inward movement thereof.

In one embodiment the blocking members are attached to the needle tip protector first portion sidewall at a proximal end of the blocking member. The blocking members can have distal ends formed to provide a locking action when mutually engaged.

In one embodiment, the needle tip protector further comprises a slip ring arranged such that on withdrawal of the inner needle, the slip ring is caused to slide over the blocking members to move the blocking members inwardly. The blocking members can be attached to the needle tip protector first portion sidewall at a proximal end of the blocking member. The blocking members can have distal ends formed to provide a locking action when mutually engaged. In one embodiment, the blocking members are attached to the needle tip protector first portion sidewall at a distal end of the blocking member. In one embodiment, two of said blocking members have proximal ends forming a tongue and groove interrelation.

BRIEF DESCRIPTION OF THE DRAWINGS

The present disclosure will now be described, by way of example only, with reference to the accompanying drawings in which:

FIG. 6(a) is a plane view; (b) is a side view; (c) is a front view; (d) is an inner side view; and (e) is a bottom view;

DETAILED DESCRIPTION OF EMBODIMENTS

Figure 1:
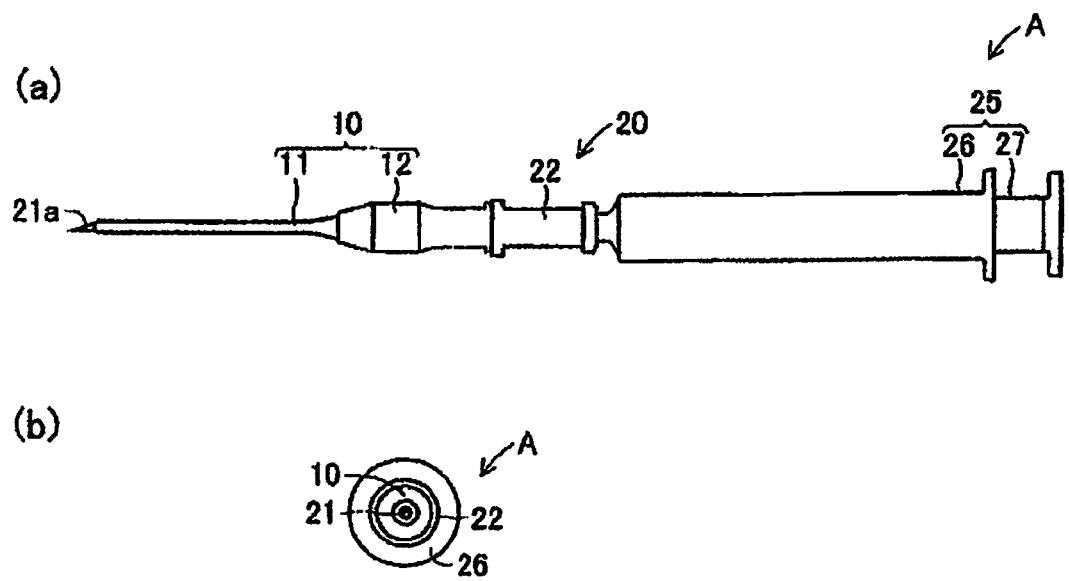
FIG. 1 shows the indwelling needle of Embodiment 1 (a) is a side view, and (b) is a front view.
Figure 2:
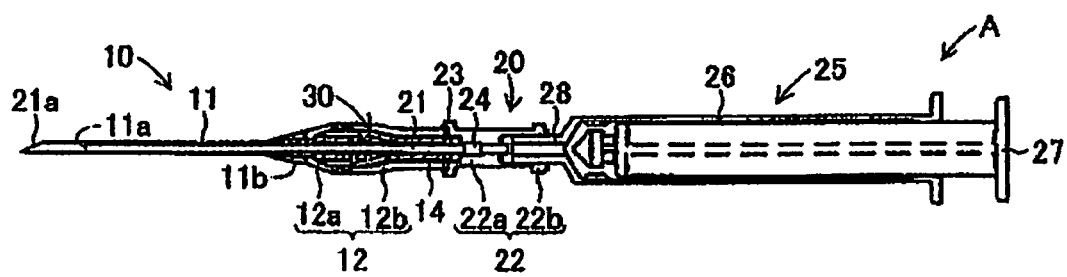
FIG. 2 is a cross-sectional view of the indwelling needle.

In the following, a detailed explanation will be given regarding embodiments of the indwelling needle of the present disclosure with reference to the figures. FIGS. 1-5 illustrate indwelling needle A in embodiment 1 of the present disclosure. Indwelling needle A is composed of an external needle (10) that indwells in the blood vessel of the patient, an internal needle (20) that can be inserted into the interior of external needle (10) and has a sharp tip portion which can pierce the body of the patient, a suction part (25) mounted on the rear portion of internal needle (20), and a needle tip protective part (30) for protecting the tip portion of internal needle (20). External needle (10) is composed of a fine tubular cannula (11), and a housing (12) which is connected to the base end portion of cannula (11). Throughout this description, the right hand side in FIG. 1 refers to the rear end portion, the tip side (left hand side) of cannula (11) will be referred to as the front side, and the base end side (right hand side) of cannula (11) will be referred to as the rear side.

Cannula (11) has an internal cavity (13) that forms the flow channel that goes from the tip portion (11a) through to the rear end portion (11b). On the outer peripheral surface of tip portion (11a) of cannula (11), a taper is formed with the front end side tapered finer. Also, rear end portion (11b) of cannula (11) gradually widens. Cannula (11) indwells in the blood vessel of the patient for withdrawing blood from the blood vessel, or for feeding medicine solutions, etc., into the blood vessel. Housing (12) is composed of a housing front portion (12a) which is fixed on rear end portion (11b) of cannula (11), and a housing rear portion (12b) that forms the rear side portion of housing (12) and has a substantially cylindrical shape.

The front end portion of housing front portion (12a) has a slender shape with a smooth surface formed between the housing front portion (12a) and rear end portion (11b) of cannula (11). The front side portion of housing rear portion (12b) has the same diameter as that of the rear end portion of housing front portion (12a). Opening portion (14) forms the rear side of housing rear portion (12b) and has a smaller diameter than the front side portion of housing rear portion (12b) and a larger diameter than the front end portion of housing front portion (12a). In addition, opening portion (14) has a female luer syringe shape with a diameter gradually increasing from the front to the rear. The portion between the front side portion of housing rear portion (12b) and opening portion (14) is formed in a cylindrical shape with the diameter decreasing toward the rear side.

The interior of housing (12) defines a space (15a) with a larger inner diameter from the front side portion to nearly the central portion along the axial direction, and a space (15b) with a smaller inner diameter in the rear side portion. The portion of the inner peripheral surface of housing (12) between space (15a) gradually increases in diameter from the front portion to the rear portion along the housing front portion (12a).

Internal needle (20) is composed of metal needle (21) which is made of stainless steel and a hub (22) fixed on a base end portion of metal needle (21). In one embodiment, metal needle (21) is made of a fine tubular injection needle, with front end portion (21a) cut oblique with respect to the axial direction to form a sharp tip portion. The front side portion of metal needle (21) has a larger diameter than the rear side portion of metal needle (21). A step (21b) is formed at a boundary portion between the front side portion and the rear side portion of the metal needle (21). Metal needle (21) is configured to ensure smooth insertion when tip portion (11a) of cannula (11) is inserted into a patient's blood vessel. Metal needle (21) is inserted into external needle (10) from the rear end portion of external needle (10), such that front end portion (21a) protrudes out of the opening of tip portion (11a) of cannula (11) for use. Front end portion (21a) of metal needle (21) passes through the interior of housing (12) and the interior of cannula (11), and protrudes out of tip portion (11a) of cannula (11).

Hub (22) is fixed on metal needle (21) such that the outer peripheral portion of the rear end portion of metal needle (21) is covered. Hub (22) includes a hub main body (22a) which is fixed to metal needle (21), and a cylindrical mounting portion (22b) which is formed on rear side of hub main body (22a) and has a recess opening towards the rear side. Mounting portion (22b) has a female luer syringe shape which gradually becomes larger from the front side to the rear side.

A flange-shaped collar portion (23) is formed on the front end peripheral portion of hub main body (22a). Metal needle (21) is bonded and fixed via bonding portion (24) to hub main body (22a). In one embodiment, suction part (25) is a syringe which includes a piston part (27) which is inserted in a cylinder part (26) that can accommodate gas or liquid. A male luer syringe tip portion (28) that forms the tip portion of cylinder part (26) is inserted into mounting portion (22b) of hub (22) to assemble suction part 25 on internal needle (20).

Needle tip protective part (30) is set in housing (12) of external needle (10). As shown in FIGS. 6-9, needle tip protective part (30) is composed of main body (31) and a pair of movable gripped parts including a movable held part (32) and movable holding part (33). Main body (31) is formed in a cylindrical shape. The inner peripheral portion of the rear end portion of tip protective part 30 has a small diameter portion (31a). A step is formed between small diameter portion (31a) and a front side inner peripheral surface (31b) of tip protective part 30. This small diameter portion (31a) has a diameter which is smaller than the diameter of the tip side portion of metal needle (21) yet allows passage of the remaining portion of metal needle (21).

Window portions (34a), (34b) extend in the axial direction along main body 31 at positions which are slightly axially offset (FIG. 7) and diametrically opposed. Window portions (34a), (34b) are each formed as holes having a larger width at the front side and a smaller width at the rear side. Base end portion 32a of movable held part (32) is connected by a hinge to the rear end edge portion of window portion (34a), and base end portion (33a) of movable holding part (33) is connected by a hinge to the rear end edge portion of window portion (34b). In the state shown in FIGS. 6 and 7, when needle tip protective part (30) is set in housing (12) of external needle (10), outer side portion (32b) of movable held part (32) protrudes towards the outer side along slope surface (16) of housing (12). Held portion (32c) of tip protective part (30) diverges outwardly from base end portion (32a), and the inner surface of held portion (32c) includes a protrusion that protrudes towards the inner side of main body (31).

Figure 6:
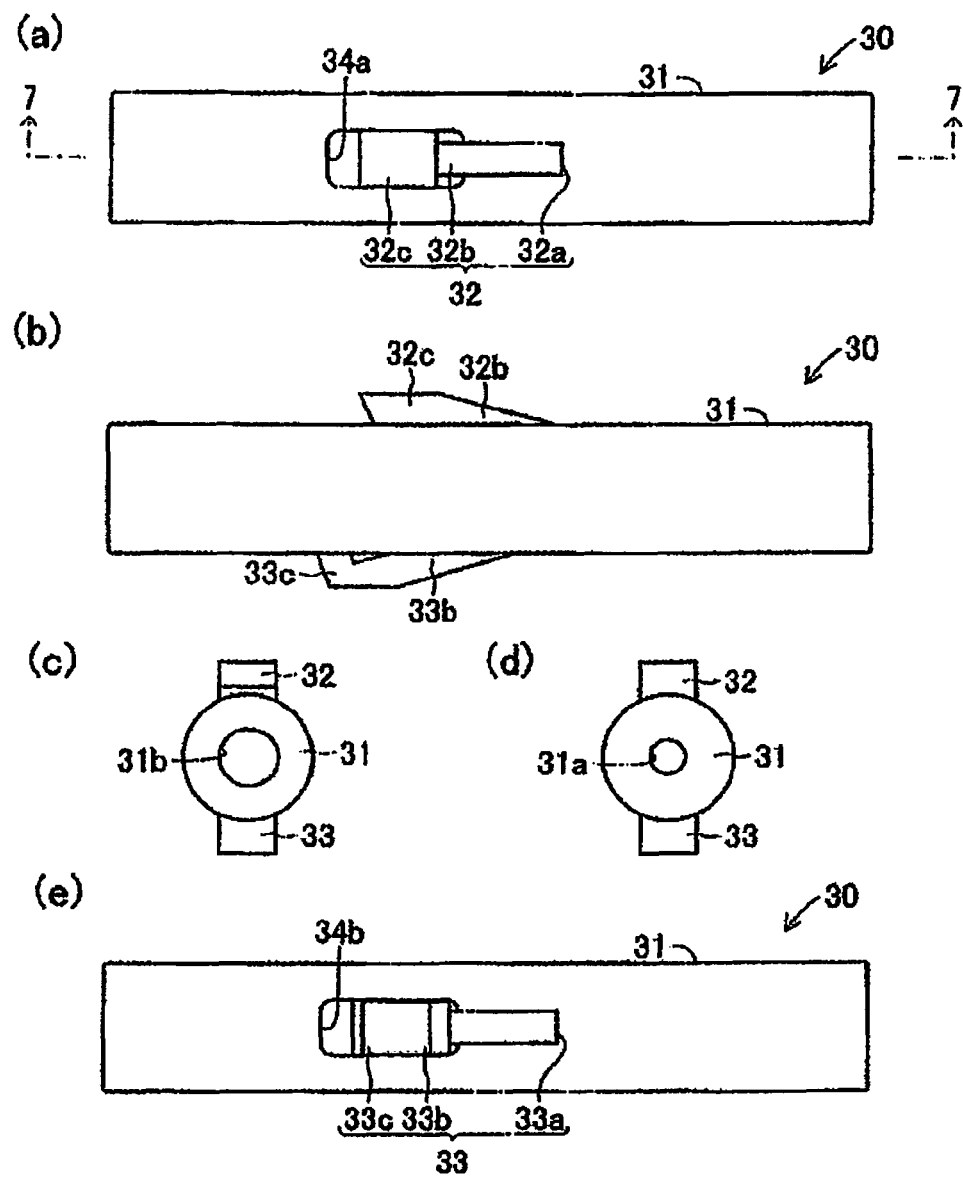
FIG. 6 illustrates the needle tip protective part in the indwelling needle in Embodiment 1.
Figure 7:
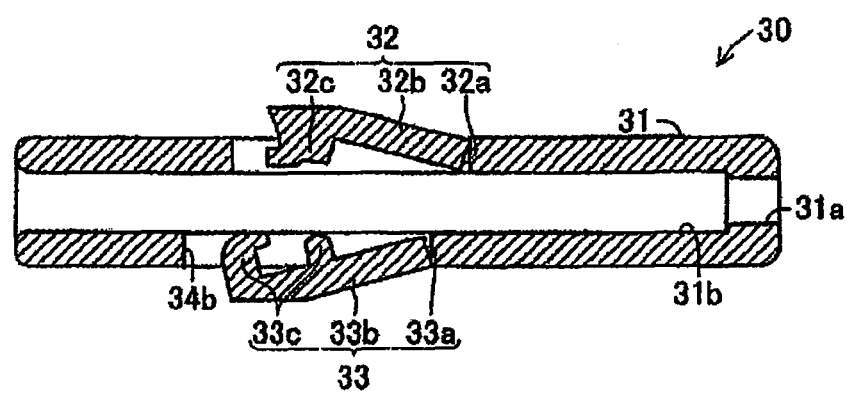
FIG. 7 is a cross-sectional view taken across 7-7 in FIG. 6(a)
Figure 8:
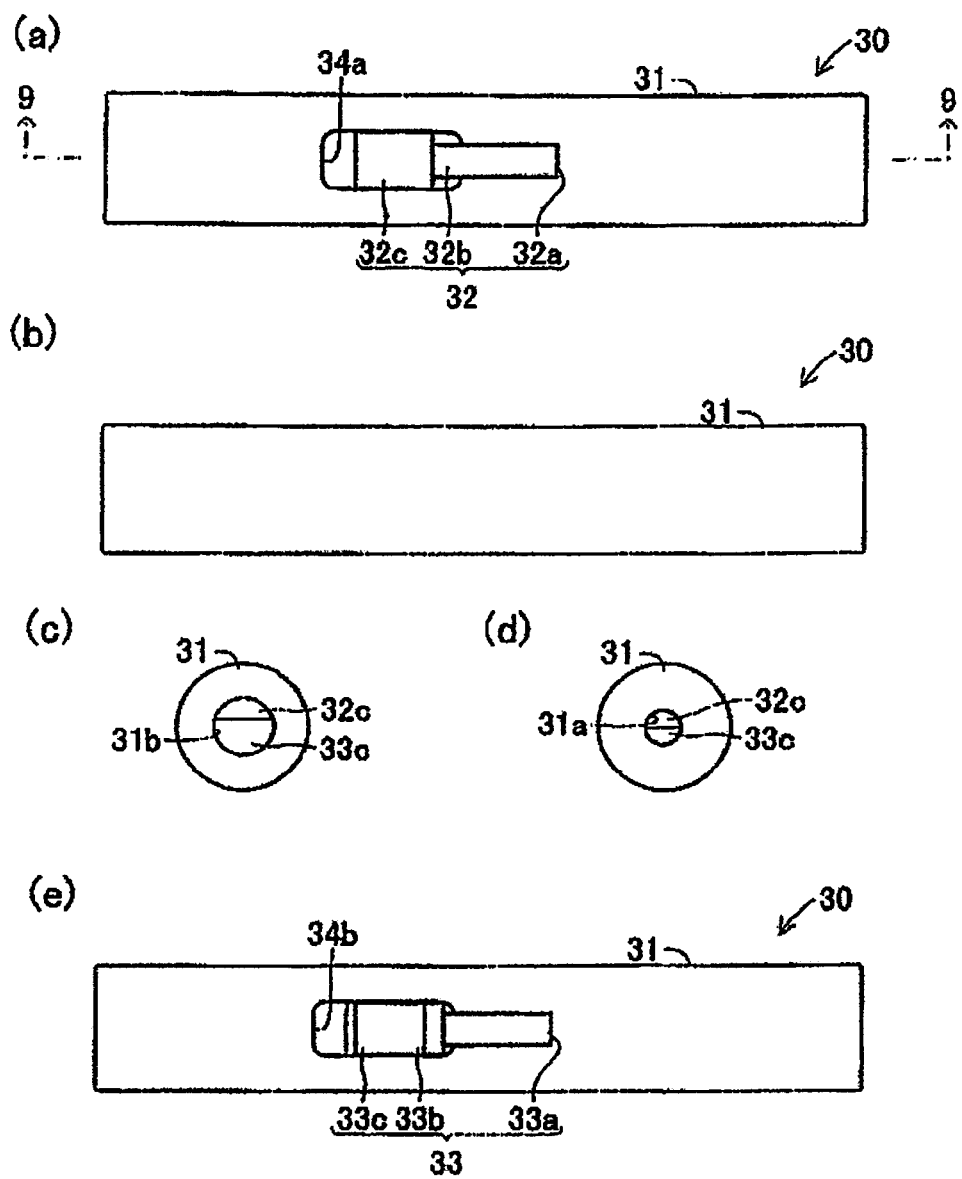
FIG. 8 illustrates the state in which the held portion and holding portion of the needle tip protective part shown in FIG. 6. (a) is a plane view; (b) is a side view; (c) is a front view; (d) is an inner side view; and (e) is a bottom view.

In the state shown in FIGS. 6 and 7, when needle tip protective part (30) is set in housing (12), outer side portion (33b) of movable holding part (33) is positioned along slope surface (16) of housing (12) and holding portion (33c) of tip protective part (30) diverges outwardly from base end portion (33a). A pair of protrusions is formed on the inner surface of holding portion (33c). The protrusions protrude towards the inner side of main body (31), and can be fixed by holding held portion (32c) of movable held part (32) from the front and back. In the state shown in FIGS. 6 and 7, metal needle (21) can be inserted through the portion inside needle tip protective part (30) corresponding to movable held part (32) and movable holding part (33).

Figure 9:
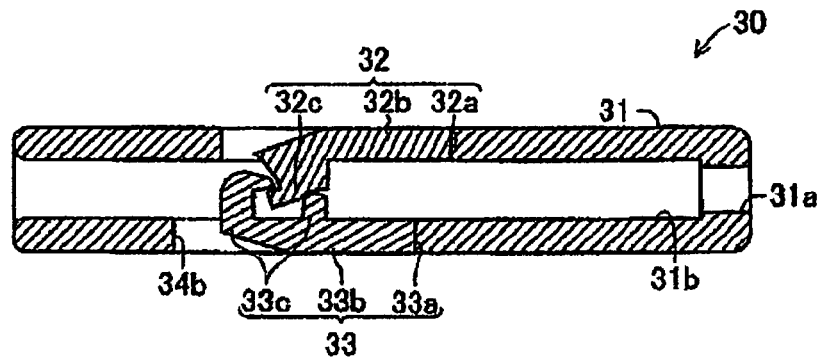
FIG. 9 is a cross-sectional view taken across 9-9 of FIG. 8(a)

When metal needle (21) is positioned inside needle tip protective part (30), held portion (32c) and holding portion (33c) are in contact with the outer peripheral surface of metal needle (21), and outer side portion (32b) of movable held part (32) and outer side portion (33b) of movable holding part (33) protrude outwardly of main body (31). When outer side portion (32b) and outer side portion (33b) are pressed into the inner side of main body (31) such that the outer surface of outer side portions (32b) and (33b) are aligned with the peripheral surface of main body (31), as shown in FIG. 9, held portion (32c) and holding portion (33c) grip or engage each other.

When metal needle (21) of internal needle (20) passes through needle tip protective part (30) set in housing (12) of external needle (10), and the rear end side of metal needle (21) is positioned inside needle tip protective part (30), front end portion (21a) of metal needle (21) extends from tip portion (11a) of cannula (11). In this case, collar portion (23) of internal needle (20) comes into contact with the rear end of opening portion (14) of housing (12) of external needle (10).

When indwelling needle A is inserted into a patient, front end portion (21a) of metal needle (21) and tip portion (11a) of cannula (11) shown in FIG. 1 are simultaneously pushed to pierce a portion of the patient, such as the wrist, to reach a blood vessel. Then, piston part (27) of suction part (25) which is attached on the rear portion of hub (22) is pulled back from cylinder part (26). As a result, the blood in the blood vessel is drawn into metal needle (21), and it enters the portion in metal needle (21) corresponding to hub main body (22a) of hub (22). Then, the blood is drawn into cylinder part (26). As a result, the color becomes red inside hub (22) and cylinder part (26), and the operator can verify that front end portion (21a) of metal needle (21) has reached the blood vessel.

Figure 3:
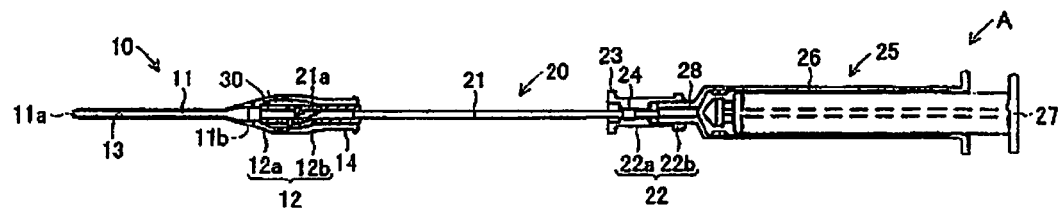
FIG. 3 is a cross-sectional view illustrating the state in which the internal needle is being pulled out of the external needle, and the movable held portion is energized to the main body side.

While internal needle (20) is maintained within the blood vessel, external needle (10) is pressed forward a little, so that tip portion (11a) of external needle (10) further enters the front portion within the blood vessel. Then, as shown in FIG. 3, internal needle (20) is pulled toward the rear side of external needle (10) with suction part (25). As this occurs, metal needle (21) is pulled from cannula (11) and front end portion (21a) of metal needle (21) is withdrawn inside needle tip protective part (30) and housing (12). Then, together with suction part (25), internal needle (20) is pulled from the rear side of external needle (10). When step (21b) of metal needle (21) engages small diameter portion (31a) of needle tip protective part (30), metal needle (21) and needle tip protective part (30) engage each other.

When needle tip protective part (30) engages the front end portion of metal needle (21), internal needle (20) together with suction part (25) and tip protective part (30) are withdrawn from external needle (10). As tip protective part (30) is withdrawn from housing (12) of external needle (10), movable held part (32) and movable holding part (33) move into engagement with slope surface (16) of housing (12) and are urged inwardly into main body (31) of tip protective part (30). As tip protective part (30) is moved from the rear end of housing (12), movable held part (32) moves towards movable holding part (33) as shown in FIG. 3

Figure 4:
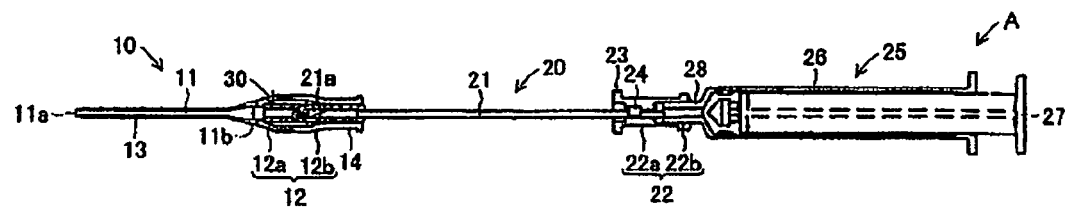
FIG. 4 is a cross-sectional view illustrating the state in which the internal needle is being pulled out of the external needle, and the movable holding portion is energized to the main body side.

When movable held part (32) and movable holding part (33) pass over slope surface (16) and enter space (15b) of housing (12), held portion (32c) and holding portion (33c) engage each other entirely. In this case, held portion (32c) of movable held part (32) and/or holding portion (33c) of movable holding part (33) are flexible, and, as the flexible portions bend, held portion (32c) and holding portion (33c) can lockingly engage each other as shown in FIGS. 4 and 9.

Figure 5:
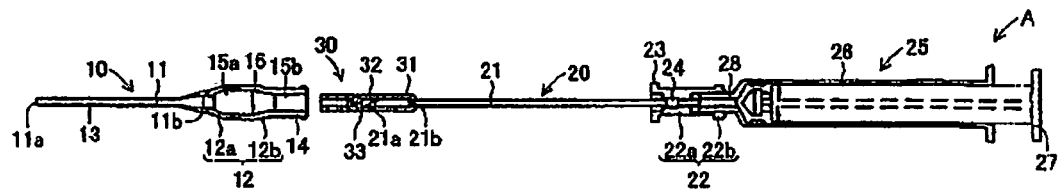
FIG. 5 is a cross-sectional view illustrating the state in which the internal needle has been pulled from the external needle.

As internal needle (20) is pulled further rearwardly with suction part (25) to the rear side of external needle (10), needle tip protective part (30) engages the tip of metal needle (21), and internal needle (20) is withdrawn together with suction part (25) from external needle (10) as shown in FIG. 5. In this case, front end portion (21a) of metal needle (21) is positioned between small diameter portion (31a) of needle tip protective part (30) and the portion of needle tip protective part (30) where held portion (32c) and holding portion (33c) lockingly engage each other. Consequently, tip protective part (30) is retained on front end portion (21a) of metal needle (21) and the likelihood of needle stick injury is minimized.

After internal needle (20) has been removed from external needle (10), a connecting portion of a tube member (not shown) which extends from a feeding device (not shown) for medicine solution or the like is connected to opening portion (14) of housing (12). In this way, while the tube member is connected to housing (12), the feeding device can deliver medicine solution, etc., to the blood vessel. Internal needle (20) which is pulled out of external needle (10) is discarded at a prescribed site.

In summary, needle tip protective part (30) includes a cylindrical main body (31), a movable held part (32) and a movable holding part (33). Movable held part (32) and movable holding part 33 are connected by a hinge to the edge portions of window portions (34a), (34b) set facing each other on the peripheral surface of main body (31). When metal needle (21) is retracted through needle tip protective part (30), movable held part (32) and movable holding part (33) are urged inwardly towards the outer side of main body (31) by slope surface (16) of housing 12 of internal needle (10). The structure is such that when needle tip protective part (30) is pulled out of housing (12), held portion (32c) of movable held part (32) and holding portion (33c) of movable holding part (33) grip or lockingly engage each other, and the front end portion of main body (31) of tip protective part (30) is obstructed. Thus, even when needle tip protective past (30) is moved to the rear side of internal needle (20) so that front end portion (21a) of needle 21 is exposed, by bringing front end portion (21a) into contact with the gripping portion between held portion (32c) and holding portion (33c), front end portion (21a) of needle (21) is prevented from becoming exposed.

The resistance to internal needle (20) is the only reactive force acting from slope surface (16) of housing (12) when movable held part (32) and movable holding part (33) are urged into main body (31). Consequently, smooth operation can be performed. Also in this case, it is only required that movable held part (32) and movable holding part (33) be connected in a rotatable way to the edge portions of window portions (34a), (34b), so that the connection can be performed even without elastic and other characteristics. Also, movable held part (32) and movable holding part (33) can be formed integrally to main body (31) by means of integrated molding. Consequently, the structure of needle tip protective part (30) becomes simpler, and manufacturing can be performed easily and with a high stability.

Embodiment 2

Figure 10:
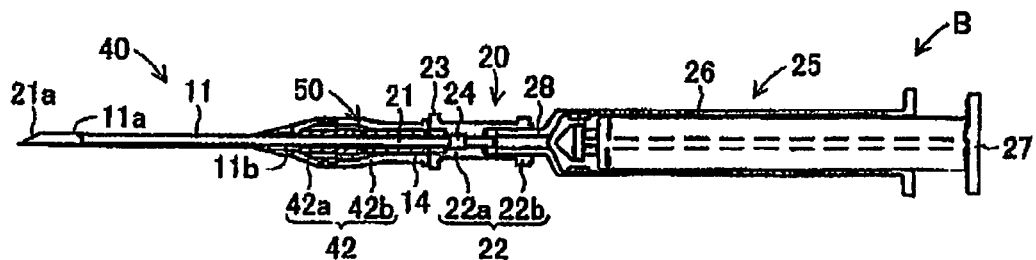
FIG. 10 is a cross-sectional view of the indwelling needle in Embodiment 2 of the present disclosure.
Figure 11:
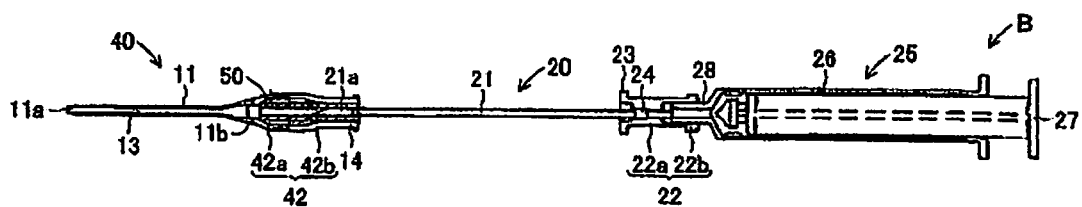
FIG. 11 is a cross-sectional view illustrating the state in which the internal needle is being pulled from the external needle of the indwelling needle shown in FIG. 10, and the held portion and the holding portion grip each other.
Figure 12:
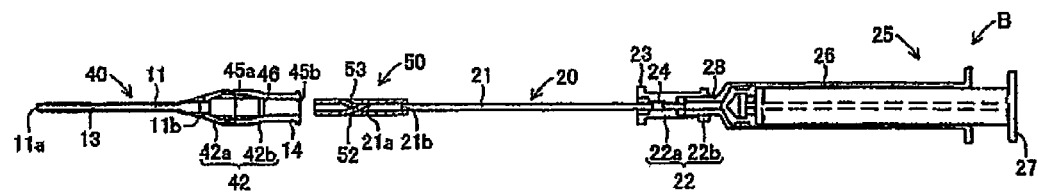
FIG. 12 is a cross-sectional view illustrating the state in which the internal needle has been pulled from the external needle of the indwelling needle shown in FIG. 10.

FIGS. 10-12 illustrate indwelling needle B in Embodiment 2 of the present disclosure. For this indwelling needle B, housing (42) of external needle (40) includes a housing front portion (42a) that forms the front side portion of housing (42) and housing rear portion (42b) that forms the rear side portion of housing (42). Housing (42) has a substantially cylindrical shape. The interior of housing (42) defines a space (45a) with a larger inner diameter between the front side portion of housing front portion (42a) to nearly the center of housing rear portion (42b). The rear side portion of housing (42) defines a space (45b) with an inner diameter smaller than that space (45a) of the front side portion. Space (45b) is formed such that its inner diameter gradually increases from the front side to the rear side. A tapered slope surface (46), short in the axial direction, is formed between space (45a) and space (45b) on the inner peripheral surface of housing (42).

As shown in FIGS. 13-16, needle tip protective part (50) of indwelling needle B is composed of main body (51), a movable held part (52) and a movable holding part (53). Main body (51) has a cylindrical shape, and the inner peripheral surface of its rear end portion (the end portion positioned on the rear end opening side when it is set in housing (42)) is formed with a diameter smaller than the remaining portion to form small diameter portion (51a). A step is formed between small diameter portion (51a) and the remaining front-side peripheral surface (51b). Window portions (54a), (54b) extend in an axial direction on main body 51 and are diametrically opposed to each other at a location a little ahead of the center in the axial direction of main body (51). Both window portions (54a), (54b) are formed as rectangular holes.

Base end portion (52a) of movable held part (52) is connected by a hinge to the front end edge portion of window portion (54a), and base end portion (53a) of movable holding part (53) is connected by a hinge to the front end edge portion of window portion (54b). In the state shown in FIGS. 13 and 14, outer side portion (52b) of movable held part (52) protrudes outwardly from main body (51) along slope surface (46) of housing (42). Held portion (52c) of the rear end (free end) is formed as a protrusion with a width which is narrower than that of movable held part (52).

Figure 13:
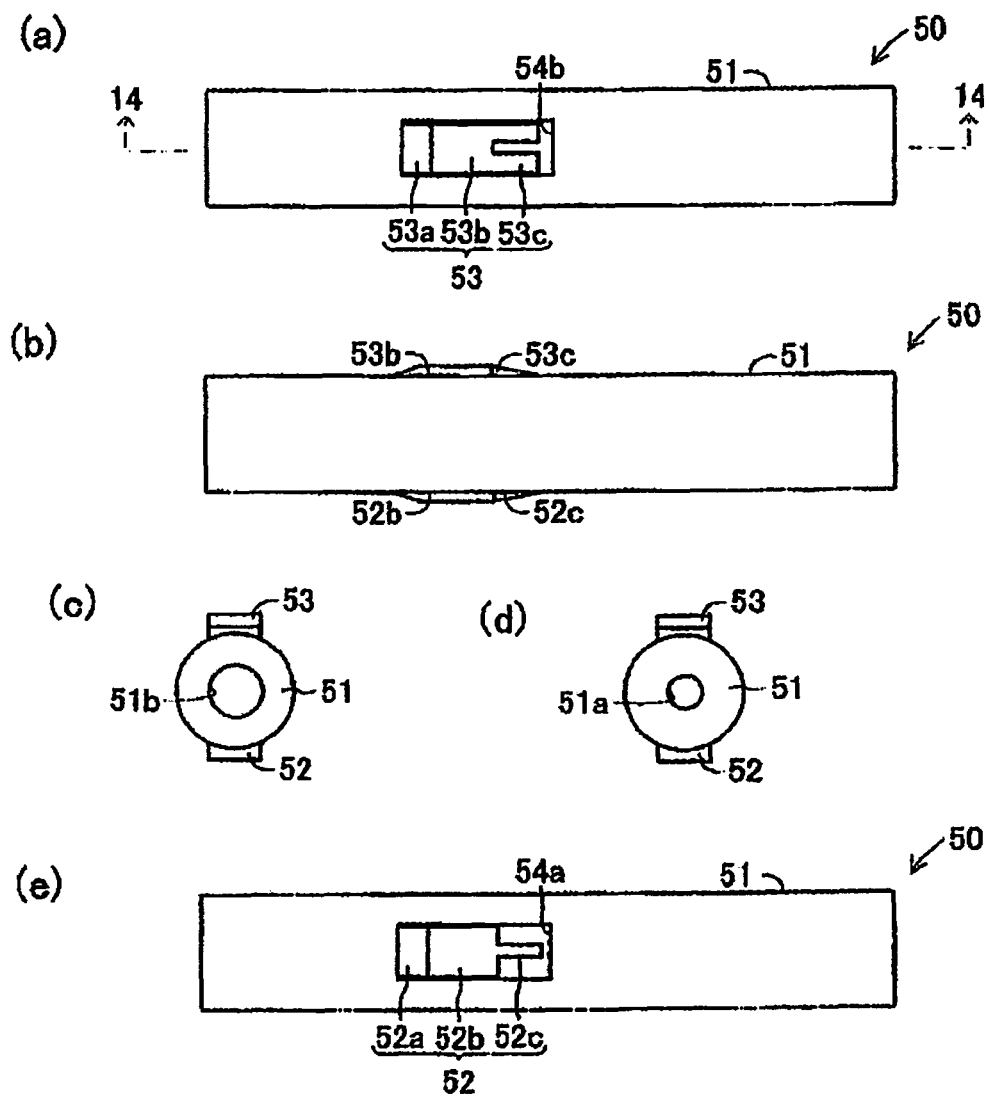
FIG. 13 illustrates the needle tip protective part of the indwelling needle in Embodiment 2. (a) is a plane view; (b) is a side view; (c) is a front view; (d) is an inner side view; (e) is a bottom view.
Figure 14:
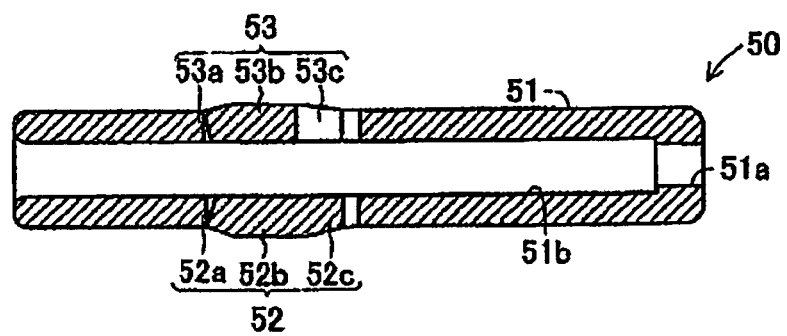
FIG. 14 is a cross-sectional view taken across 14-14 in FIG. 13(a)
Figure 15:
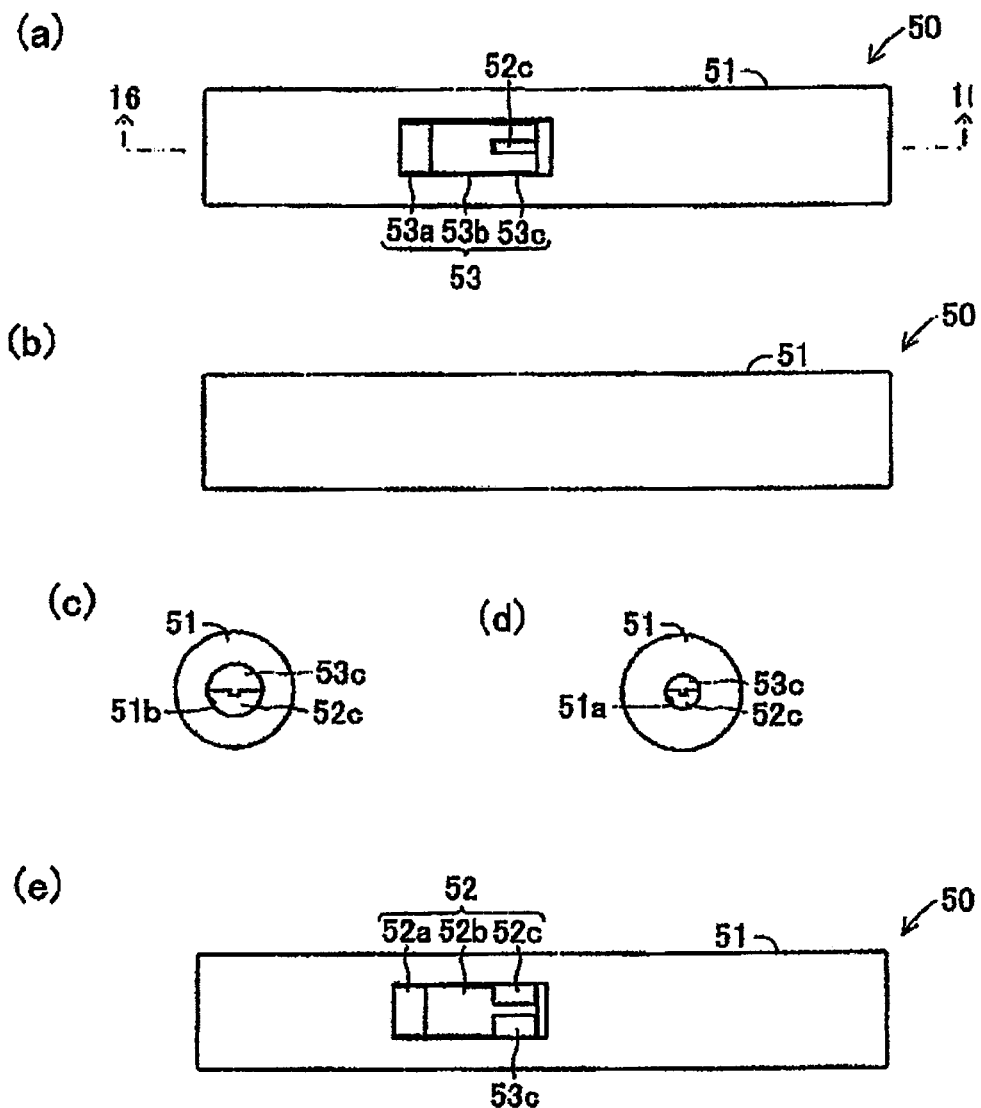
FIG. 15 illustrates the state in which the held portion and holding portion of the needle tip protective part shown in FIG. 13 grip each other, (a) is a plane view; (b) is a side view; (c) is a front view; (d) is an inner side view; (e) is a bottom view.
Figure 16:
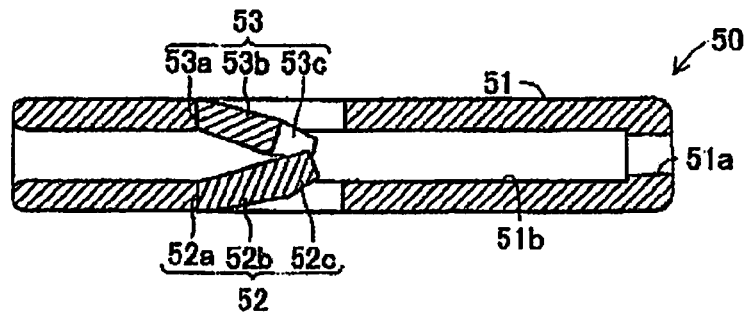
FIG. 16 is a cross-sectional view taken across 16-16 of FIG. 15(a)

In the state shown in FIGS. 13 and 14, outer side portion (53b) of movable holding part (53) protrudes outwardly from main body (51) towards slope surface (46) of housing (42). Holding portion (53c) on the rear end of movable holding part (53) is formed as a pair of protrusions formed by providing a recess that has the rear side and upper/lower sides open at the center in the width direction. This holding portion (53c) is formed such that held portion (52c) of movable held part (52) can be received and retained in the recess in holding portion (53c). As shown in FIGS. 14 and 16. The structure of the remaining portion of indwelling needle B is the same as that in indwelling needle A. Consequently, the same part numbers as those adopted for indwelling needle A are adopted, and they will not be explained again.

When indwelling needle B is in use, the same operation as that for indwelling needle A is performed. In this case after front end portion (21a) of metal needle (21) is inserted through tip portion (11a) of cannula (11) in indwelling needle B as shown in FIG. 10, cannula (11) and needle (21) are simultaneously pushed to pierce the wrist of the patient to reach the blood vessel. Next, external needle (10) is pushed a little more to the front side so that tip portion (11a) of external needle (10) reaches the blood vessel. While tip portion (11a) of external needle (10) indwells in the blood vessel of the patient as shown in FIG. 11, internal needle (20) is pulled towards the rear side of external needle (10) together with suction part (25). Metal needle (21) is withdrawn from cannula (11) and front end portion (21a) of metal needle (21) is positioned in needle tip protective part (50) in housing (42). Then, internal needle (20) is pulled towards the rear side of external needle (40) such that step (21b) of metal needle (21) and small diameter portion (51a) of needle tip protective part (50) engage or grip each other.

Together with suction part (25), internal needle (20) is pulled back to the rear side of external needle (10). As a result, while needle tip protective part (50) engages the front end portion of metal needle (21), internal needle (20) is withdrawn together with suction part (25) from external needle (10). When metal needle (21) is still positioned in the portion inside needle tip protective part (50) corresponding to movable held part (52) and movable holding part (53), by means of metal needle (21), movable held part (52) and movable holding part (53) are urged inwardly of main body (51) as they move along slope surface (46) within housing (42). As needle tip protective part (50) engages metal needle (21), metal needle (21) and needle tip housing are withdrawn from housing (42). As a result, outer side portion (52b) of movable held part (52) and outer side portion (53b) of movable holding part (53) are urged by slope surface (46) towards the inner side of main body (51) as shown in FIG. 11.

When movable held part (52) and movable holding part (53) move over slope surface (46) and enter space (45b) of housing (42), held portion (52c) and holding portion (53c) are engaged. Then, as internal needle (20) is withdrawn with suction part (25) to the rear side of external needle (10), while needle tip protective part (50) is engaged with the tip of metal needle (21), internal needle (20) is withdrawn with suction part (25) from external needle (10) as shown in FIG. 12. Thereafter, a connecting portion of a tube member extending from a feeding device for delivering medicine solution or the like is connected to opening portion (14) of housing (42). In this way, the feeding device which is connected to the base end portion of the internal needle can operate to deliver medicine solution, etc., to the blood vessel.

Referring to FIGS. 13-14, held portion (52c) is formed on the rear end portion of movable held part (52), and holding portion (53c) is formed on the rear end portion of movable holding part (53). Consequently, the distance between the portion where held portion (52c) and holding portion (53c) are engaged and the front end portion of main body (51) becomes longer and front end portion (21a) of metal needle (21) moves away from the front end portion of main body (51). As a result, front end portion (21a) of metal needle (21) can barely exit the front end portion of needle tip protective part (50). Also, when needle tip protective part (50) is moved to the rear side of internal needle (20) so as to expose front end portion (21a) of metal needle (21), front end portion (21a) of metal needle (21) presses the gripped portion between held portion (52c) and holding portion (53c), so that the grip between held portion (52c) and holding portion (53c) is made stronger. Consequently, safety is further improved. The other functions and effects of indwelling needle B are the same as those of the indwelling needle A.

Embodiment 3

Figure 17:
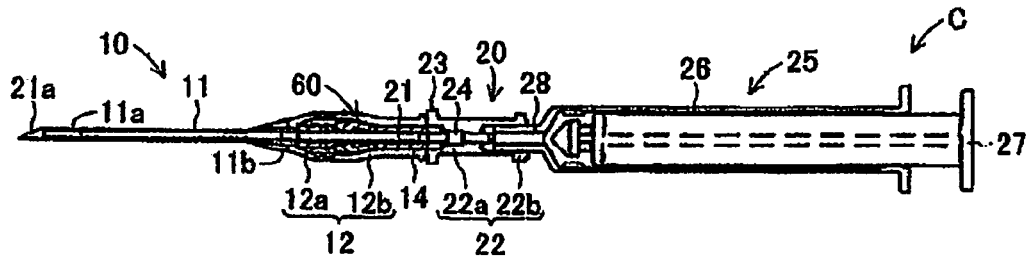
FIG. 17 is a cross-sectional view of the indwelling needle in Embodiment 3 of the present disclosure.
Figure 18:
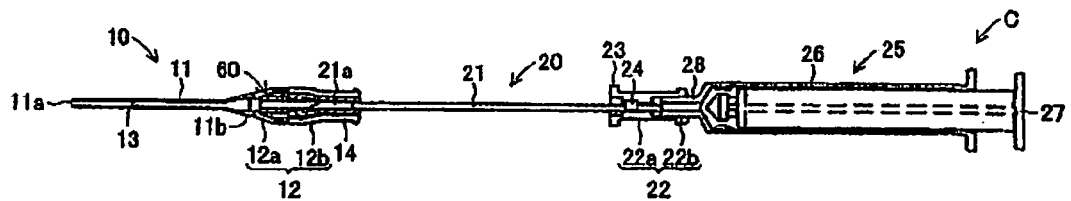
FIG. 18 is a cross-sectional view illustrating the state after the internal needle is being pulled out of the external needle in the indwelling needle shown in FIG. 17.
Figure 19:
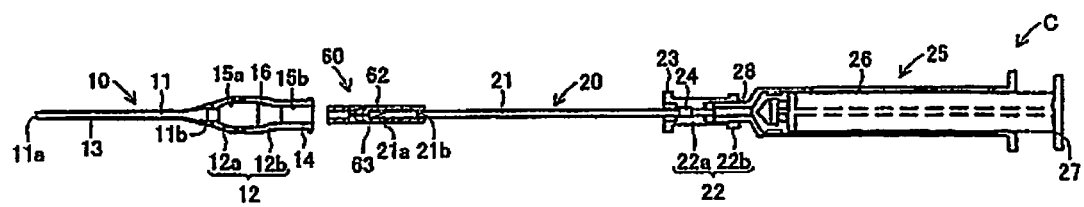
FIG. 19 is a cross-sectional view illustrating the state after the internal needle has been pulled out of the external needle in the indwelling needle shown in FIG. 17.

FIGS. 17-19 illustrate indwelling needle C in Embodiment 3 of the present disclosure. For indwelling needle C, as shown in FIGS. 20-23, needle tip protective part (60) is composed of main body (61) and a pair of movable gripped parts (62), (63). Main body (61) has a cylindrical shape, and the inner peripheral surface of its rear end portion is formed with a diameter smaller than the remaining portion to form small diameter portion (61a). A step is formed between small diameter portion (61a) and the remaining front-side peripheral surface (61b). Window portions (64a), (64b) which extend in an axial direction on main body (61) are formed in the portions facing each other at the site a little ahead of the center in the axial direction of main body (61). Both window portions 64a, 64b are formed as tapered holes wider in front and narrower toward the rear.

Figure 20:
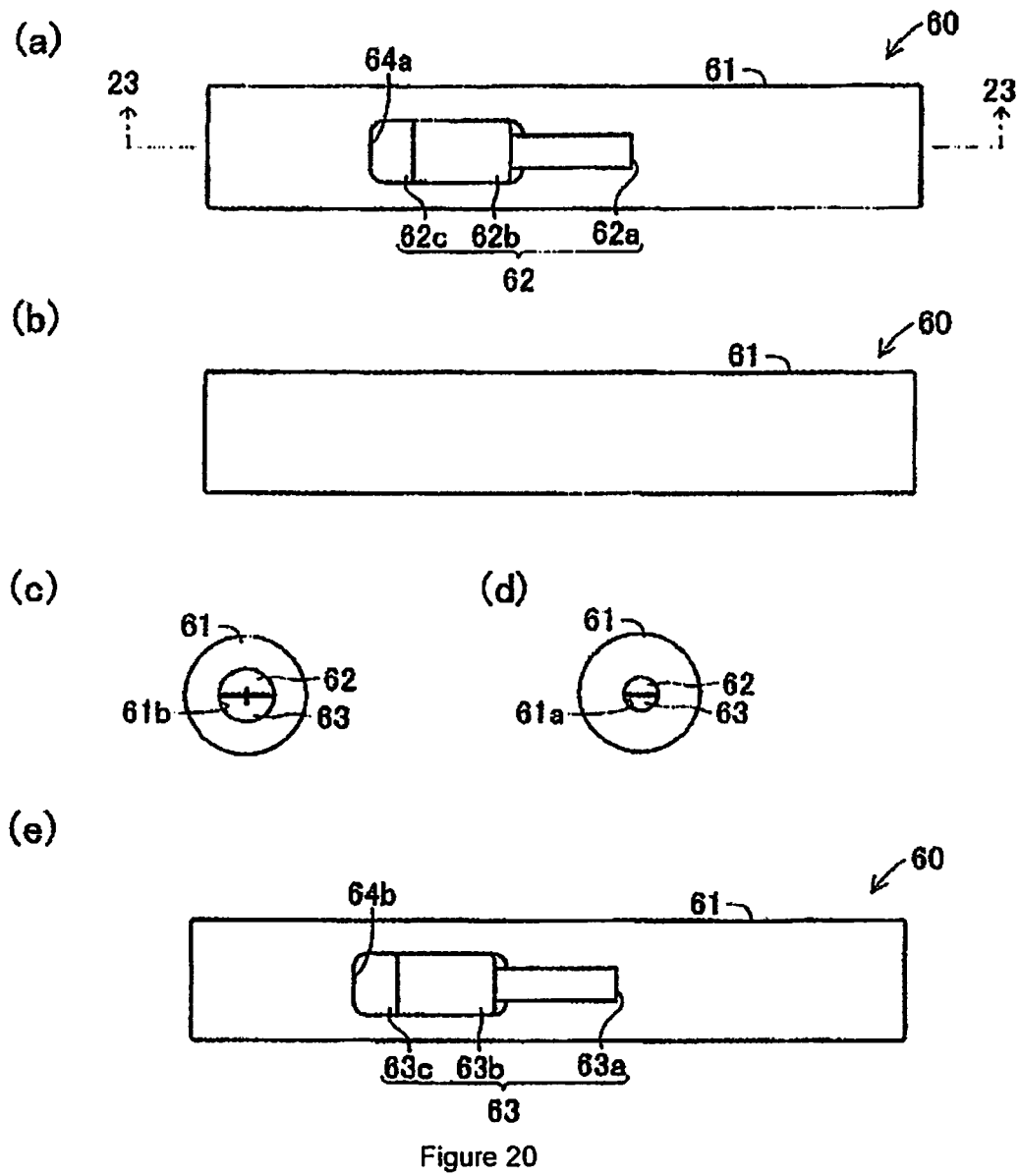
FIG. 20 illustrates the needle tip protective part of the indwelling needle in Embodiment 3. (a) is a plane view; (b) is a side view; (c) is a front view; (d) is an inner side view; (e) is a bottom view.
Figure 21:
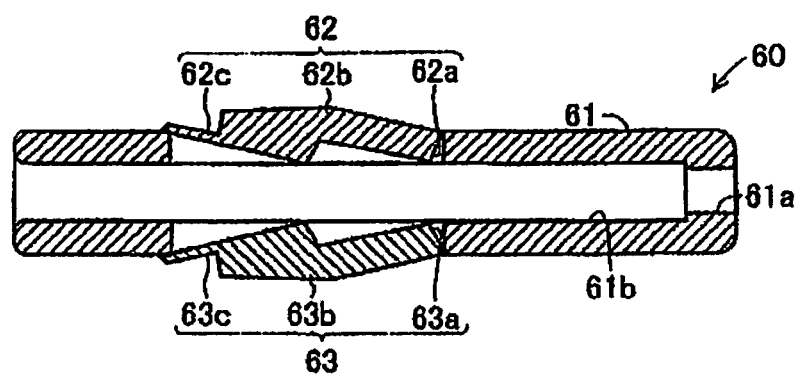
FIG. 21 is a cross-sectional view taken across 21-21 in FIG. 20(a)
Figure 22:
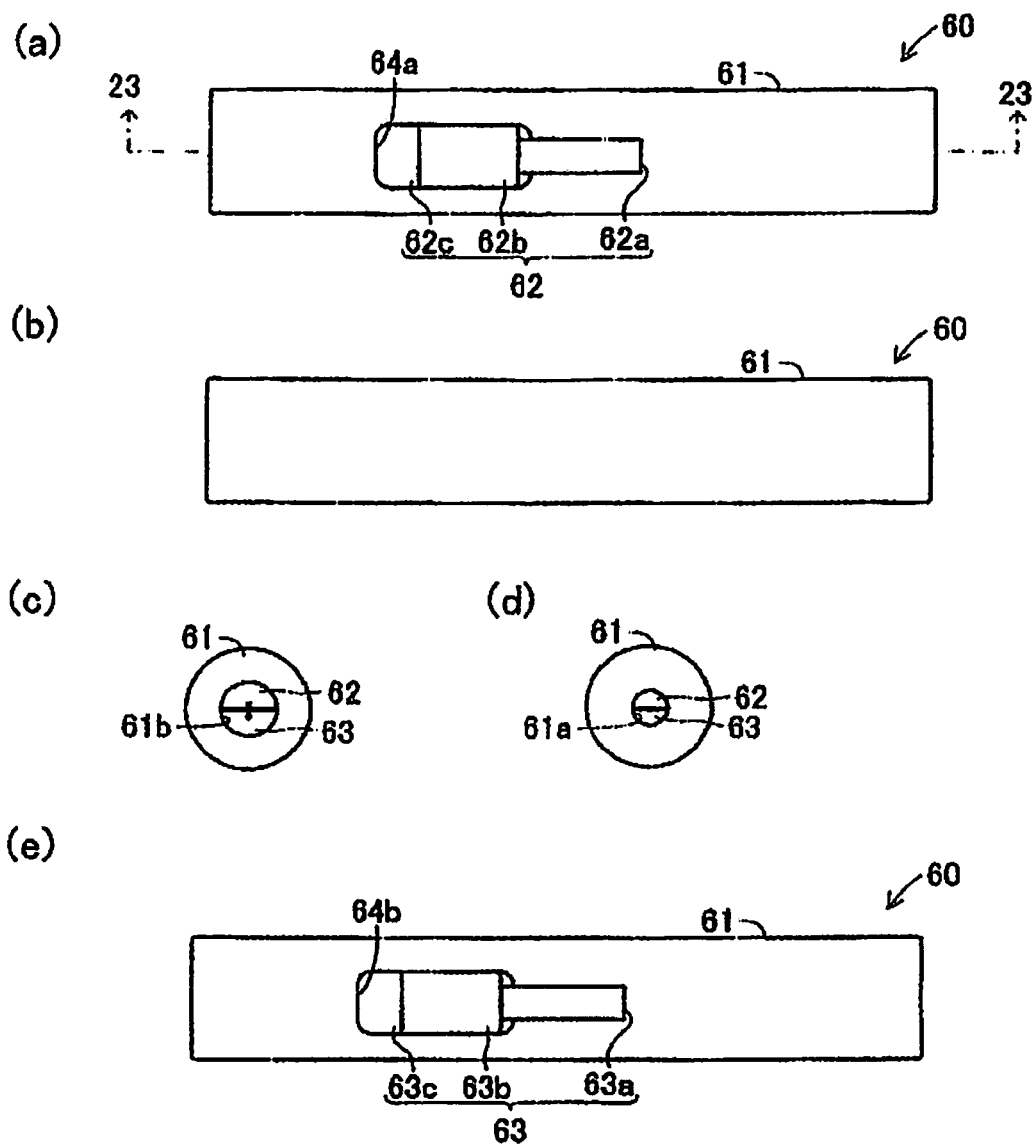
FIG. 22 illustrates the state in which the gripping pieces of the needle tip protective part shown in FIG. 20 have entered the main body, (a) is a plane view; (b) is a side view; (c) is a front view; (d) is an inner side view; (e) is a bottom view.
Figure 23:
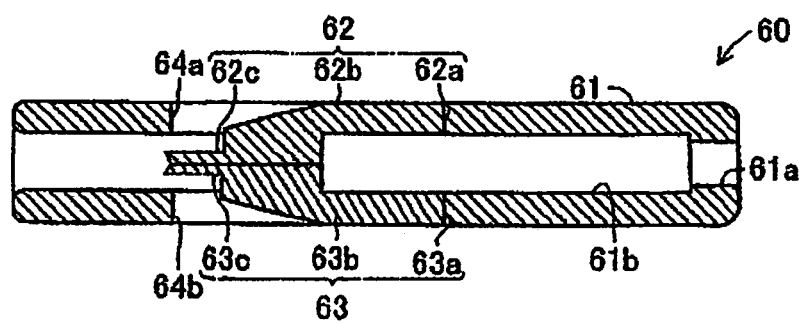
FIG. 23 is a cross-sectional view taken across 23-23 in FIG. 22(a)

Base end portion (62a) of movable held part (62) is connected by a hinge to the rear end edge portion of window portion (64a), and base end portion (63a) of movable holding part (63) is connected by a hinge to the rear end edge portion of window portion (64b). As shown in FIGS. 20 and 21, outer side portion (62b) of movable held part (62) protrudes outwardly from main body (61). A flexible planar shaped gripping piece (62c) is formed on the front end (free end) of movable gripped part (62). In the state shown in FIGS. 20 and 21, outer side portion (63b) of movable holding part (63) protrudes outwardly of main body (61). On the front end (free end) of movable gripped part (63), a flexible planar-shaped gripping piece (63c) is formed.

When the pair of movable gripped parts (62), (63) is urged towards the inner side of main body (61), the parts (62), (63) are bent while in contact with the front end edge portions of window portions (64a), (64b). The structure is such that, after gripping pieces (62c), (63c) enter main body (61), gripping pieces (62c), (63c) are obstructed from exiting the main body (61) by engagement with the front edge portions of window portions (64a), (64b). The structure of the remaining portion of the indwelling needle C is the same as that in indwelling needle A. Consequently, the same part numbers as those adopted for indwelling needle A are adopted, and they will not be explained again.

Indwelling needle C is used in a manner substantially similar to indwelling needle A as described above. Just as in the Embodiments 1 and 2, tip portion (11a) of external needle (10) indwells in the blood vessel of the patient in the state shown in FIG. 17. Thereafter, internal needle (20) is pulled together with suction part (25) to the rear side of external needle (10) as shown in FIG. 18. After front end portion (21a) of metal needle (21) is positioned in needle tip protective part (60) in housing (42), internal needle (20) is pulled towards the rear side of housing 12 such that step (21b) of metal needle (21) and the small diameter portion (61a) of needle tip protective part (60) grip or engage each other.

Then, internal needle (20) is pulled together with suction part (25) rearwardly in relation to external needle (10), while needle tip protective part (60) engages the tip side portion of metal needle (21). When metal needle (21) is positioned in the portion inside needle tip protective part (60) corresponding to movable gripped parts (62), (63), by means of metal needle (21), movable gripped parts (62), (63) are moved along slope surface (16) within housing (12). Then, as needle tip protective part (60) engages metal needle (21), metal needle (21) and protective part (60) are withdrawn from housing (12). As a result, outer side portions (62b), (63b) of movable gripped parts (62), (63) are urged into main body (61) by slope surface (16).

As a result, gripping pieces (62c), (63c) contact the front end edge portions of window portions (64a), (64b) and are bent (FIG. 21). In this state, gripping pieces (62c), (63c) enter main body (61) as internal needle (20) is withdrawn with suction part (25) to the rear side of external needle (10), as shown in FIG. 19. Thereafter, a connecting portion of a tube member extending from a feeding device can be operated to deliver medicine solution or the like to opening portion (14) of housing (12). In this way, the feeding device can be operated to deliver medicine solution, etc., to a blood vessel.

For indwelling needle C, when gripping pieces (62c), (63c) of the pair of movable gripped parts (62), (63) engage the edge portions of window portions (64a), (64b), the interior of main body (61) is obstructed while the gap formed between the pair of movable gripped parts (62), (63) becomes smaller than the diameter of metal needle (21). Consequently, there is no need to have the gripping pieces (62c), (63 c) grip each other, and the force for urging the pair of movable gripped parts (62), (63) into main body (61) can be small. The other functions and effects of indwelling needle C are the same as those of indwelling needle A as described above.

Embodiment 4

Figure 24:
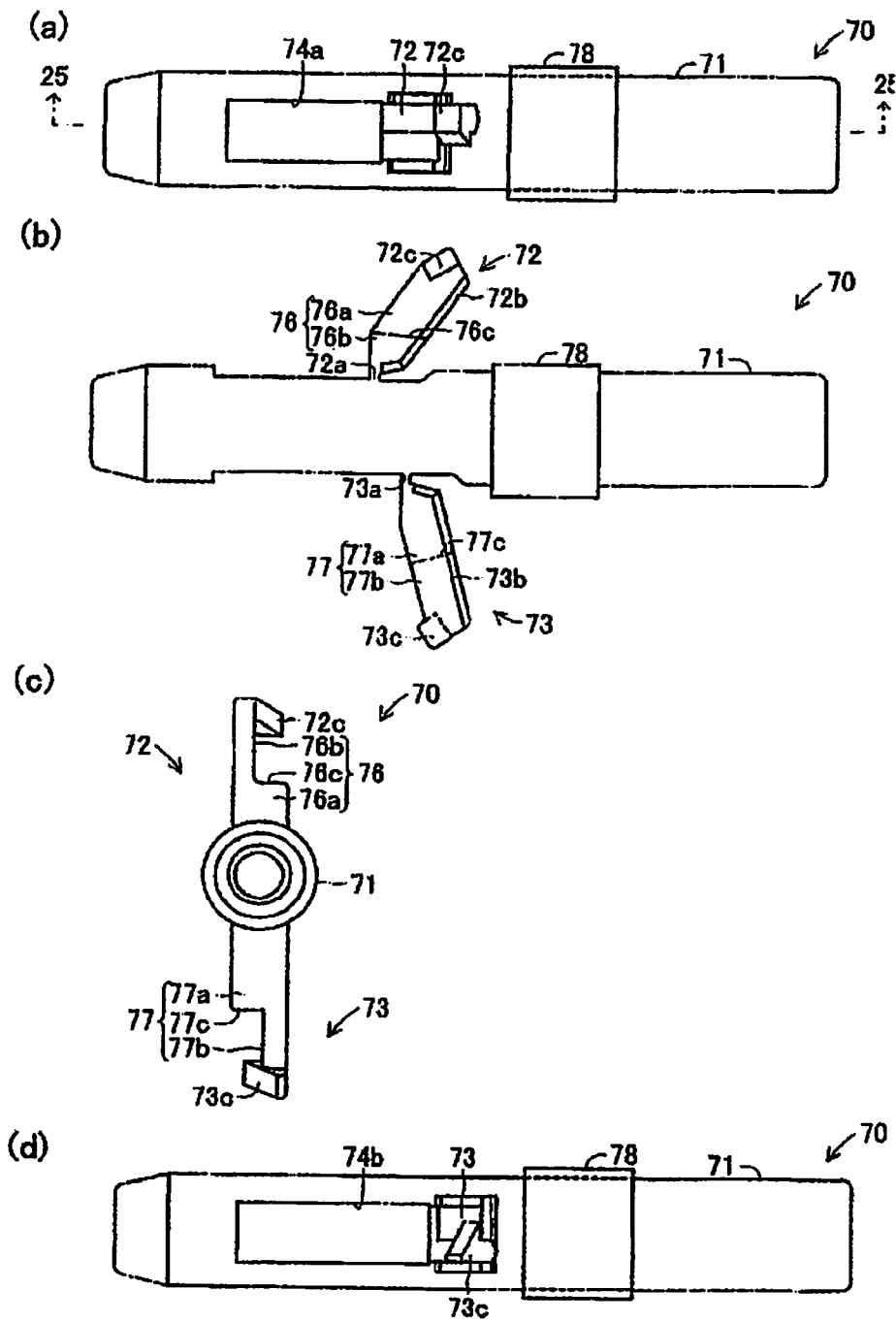
FIG. 24 is a diagram illustrating the needle tip protective part of the indwelling needle in Embodiment 4. (a) is a plane view; (b) is a side view; (c) is a front view; (d) is an inner side view.
Figure 25:
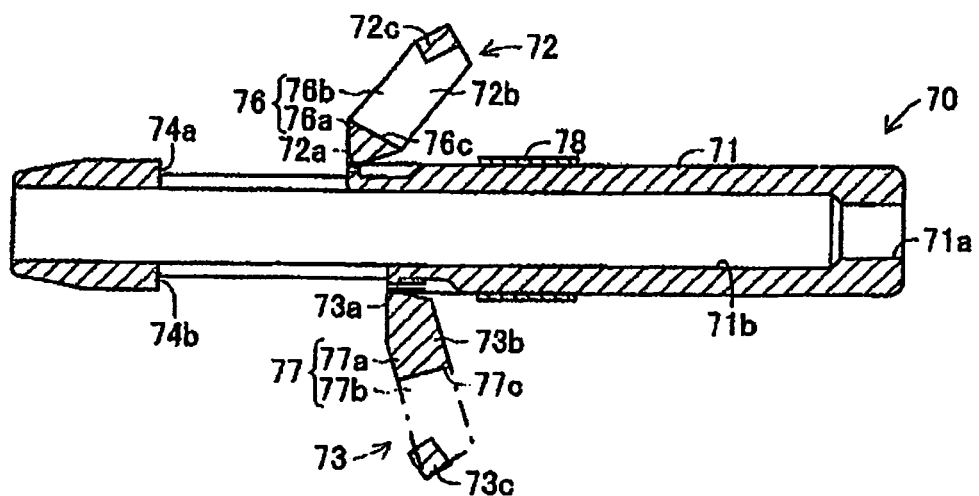
FIG. 25 is a cross-sectional view taken across 25-25 of FIG. 24(a)

FIGS. 24 and 25 illustrate needle tip protective part (70) of the indwelling needle in Embodiment 4 of the present disclosure. The needle tip protective part (70) is composed of main body (71) and a pair of movable gripped parts (72), (73). Main body (71) has a cylindrical shape, and the inner peripheral surface of its rear end portion (the right hand side end portion shown in FIGS. 24 and 25) is formed with a diameter smaller than the remaining portion to form small diameter portion (71a). A step is formed between small diameter portion (71a) and the remaining front-side peripheral surface (71b). Window portions (74a), (74b) which extend in the axial direction on main body (71) are formed in the portions facing each other at a location a little ahead of the center of main body (71) in the axial direction of main body (71). Both window portions (74a), (74b) are formed as rectangular holes with different lengths in the longitudinal direction. While these window portions have front end portions positioned at the same site in the axial direction, their rear end portions are located at different positions. More specifically, the rear end portion of window portion (74b) is positioned behind that of window portion (74a).

Base end portion (72a) of movable held part (72) is connected by a hinge to the rear end edge portion of window portion (74a), and base end portion (73a) of movable holding part (73) is connected by a hinge to the rear end edge portion of window portion (74b). Main body (76) of the gripping portion of movable gripped part (72) is composed of a thicker portion (76a) on the side of base end portion (72a), and a thinner portion (76b) on the tip side. The width of thicker portion (76a) is selected to be smaller than that of window portion (74a). The width of thinner portion (76b) is selected to be smaller than that of window portion (74a) such that thinner portion (76b) is positioned along the center of window portion (74a) in the width direction.

Figure 26:
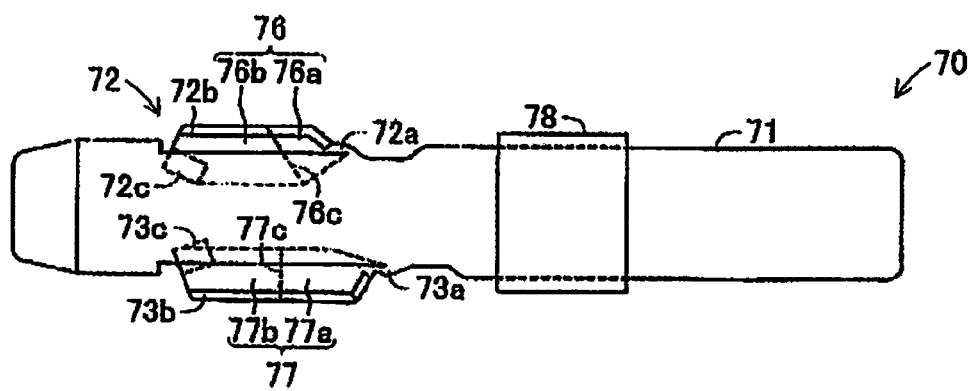
FIG. 26 is a side view illustrating the state in which the ring-shaped member is positioned on the rear side of the main body.

Step (76c) is formed at the boundary between thicker portion (76a) and thinner portion (76b) on one surface of main body (76) of the gripping portion. The thickness of thinner portion (76b) is selected to be a little smaller than half the thickness of thicker portion (76a). As shown in FIG. 26, outer side portion (72b) of movable gripped part (72) protrudes outwardly of main body (71). A wedge-shaped gripping protrusion (72c) is formed on the surface on the side of step (76c) in thinner portion (76b) of the main body (76) of the gripping portion of movable gripped part (72).

Main body (77) of the gripping portion of movable gripped part (73) is composed of a thicker portion (77a) on the side of base end portion (73a) and a thinner portion (77b) on the tip side. The width of thicker portion (77a) is selected to be a little smaller than that of window portion (74b). The width of thinner portion (77b) is selected to be smaller than window portion (74b) so that thinner portion (77b) is located at nearly the center of window portion (74b) in the width direction. Step (77c) is formed at the boundary portion between thicker portion (77a) and thinner portion (77b) on the other surface of main body (77) of the gripping portion. The thickness of thinner portion (77b) is selected to be a little smaller than half the thickness of thicker portion (77a). As shown in FIG. 26, outer side portion (73b) of movable gripped part (73) protrudes outwardly of main body (71) of protective tip (70). On the surface on the side of step (77c) in thinner portion (77b) of main body (77) of the gripping portion, a wedge-shaped gripping protrusion (73c) is provided that can be gripped or engaged by gripping protrusion (72c) of movable gripped part (72).

On the outer peripheral surface of main body (71), a ring-shaped member (78) is attached such that it can move in the axial direction of main body (71). As shown in FIGS. 26-31, as ring-shaped member (78) is moved from the rear end side to the front end side of main body (71), movable gripped parts (72), (73) can pass through the interior of window portions (74a), (74b) and can be pressed into main body (71). On the rear end of housing (12) of the external needle (10) having needle tip protective part (70) attached to it, a recess (not shown in the figure) for fixing ring-shaped member (78) is formed. The other features of the structure of the indwelling needle having the needle tip protective part (70) are the same as those of the indwelling needle A, and the same part numbers are adopted here.

Figure 27:
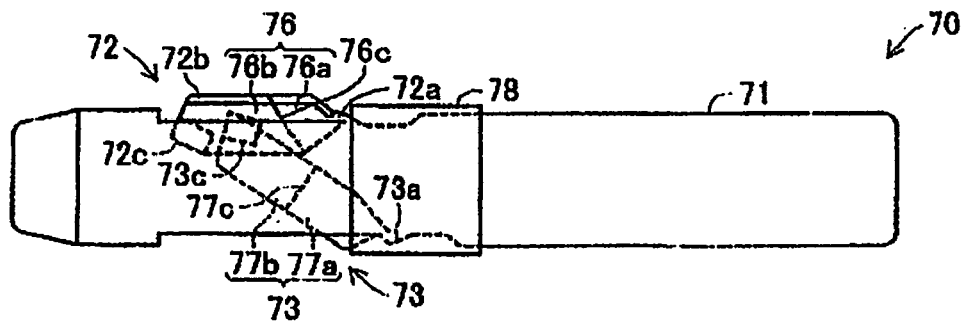
FIG. 27 is a side view illustrating the state in which the ring-shaped member is moved to the front side of the main body, and one movable gripped part is energized in the main body.

The operation of movable gripped parts (72), (73) in the indwelling needle having needle tip protective part (70) can be explained with reference to FIGS. 26-31. In use, ring-shaped member (78) is moved to the front side of main body (71), as shown in FIG. 27. As a result, after the front end portion of ring-shaped member (78) comes into contact with base end portion (73a) of movable gripped part (73), movable gripped part (73) is pressed ahead. As a result, movable gripped part (73) rotates around base end portion (73a) and it enters main body (71). In this case, as shown in FIG. 27, thinner portion (77b) and wedge-shaped gripping protrusion (73c) of movable gripped part (73) move to enter the recess side portion of thinner portion (76b) of movable gripped part (72).

Figure 28:
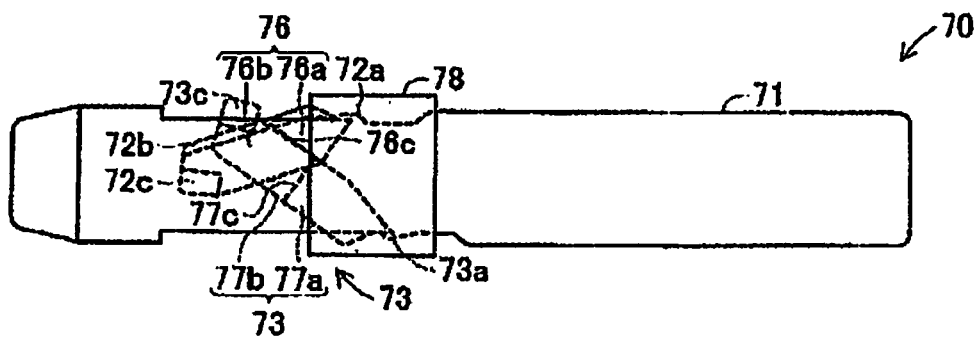
FIG. 28 is a side view illustrating the state in which the ring-shaped member is moved to the front side of the main body, and the pair of movable gripped parts are energized in the main body.
Figure 29:
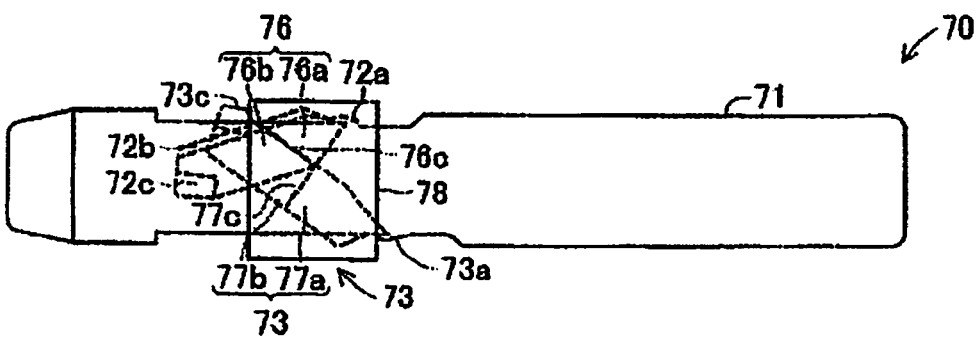
FIG. 29 is a side view illustrating the state in which the ring-shaped part is further moved, and the pair of movable gripped parts are energized in the main body.
Figure 30:
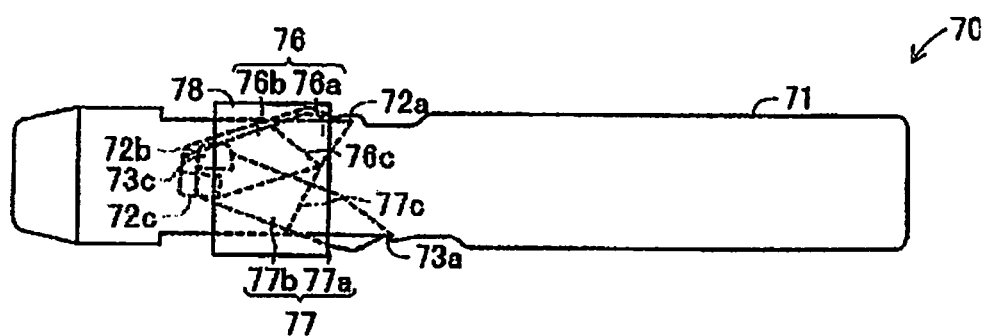
FIG. 30 is a side view illustrating the state in which the ring-shaped part is made to pass through the portion corresponding to the pair of movable gripped parts in the main body, and the pair of movable gripped parts is gripped.

When ring-shaped member (78) is moved further towards the front side of main body (71), after the tip portion of ring-shaped member (78) comes into contact with base end portion (72a) of movable gripped part (72), it presses movable gripped part (72) forward. As a result, movable gripped part (72) rotates around base end portion (72a) and, as shown in FIG. 28, it enters main body (71). Gripping protrusion (72c) of movable gripped part (72) moves so that it detours to the outer side of wedge-shaped gripping protrusion (73c) of movable gripped part (73). As shown in FIG. 29, the rear end portion of ring-shaped member (78) passes through the portion of main body (71) corresponding to base end portion (72a) of movable gripped part (72). Then, the rear end portion of ring-shaped member (78) is made to pass through the portion of main body (71) corresponding to outer side portion (72b) of movable gripped part (72) as shown in FIG. 30.

Figure 31:
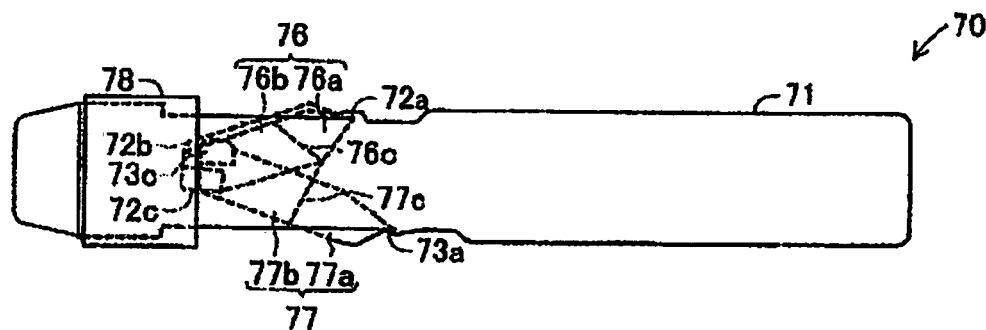
FIG. 31 is a side view illustrating the state in which the ring-shaped member is moved to the front side of the main body, and the gripping state of the pair of the movable gripped parts is maintained.

As a result, gripping protrusion (72c) of movable gripped part (72) and gripping protrusion (73c) of movable gripped part (73) become located near the central axis of main body (71), and their positions in the axial direction are nearly the same. Consequently, gripping protrusion (72c) and gripping protrusion (73c) grip or engage each other. As shown in FIG. 31, even when ring-shaped member (78) is moved to the front side of main body (71), the gripping state between gripping protrusion (72c) and gripping protrusion (73c) is maintained. That is, the gripping state of gripping protrusion (72c) and gripping protrusion (73 c) is maintained as long as the gripping position is not positioned away from the central axis of main body (71) over a prescribed distance.

The length of ring-shaped member (78) in the axial direction is increased, and as shown in FIG. 31, the rear end portion of ring-shaped member (78) can also be located behind the gripping position between gripping protrusion (72c) and gripping protrusion (73c). As a result, even when gripping protrusion (72c) and gripping protrusion (73c) are disengaged from each other, because movable gripped parts (72), (73) are covered by ring-shaped member (78), they do not protrude outwardly of main body (71). Consequently, the needle tip of the internal needle can be protected and the stability becomes even higher. The operation for using the indwelling needle having needle tip protective part (70) is the same as that in the previously described embodiments, and will not be explained in detail again. Also, the same functions and effects as those in the previously described embodiments can be realized for the indwelling needle having needle tip protective part (70).

The indwelling needles of the present disclosure are not limited to the aforementioned embodiments. One can make appropriate modifications to the embodiments. For example, in the embodiments, external needle (10) of indwelling needle A or the like indwells in the blood vessel. However, the sites for indwelling for the indwelling needle of the present disclosure are not limited to blood vessels. They also include other areas in a patient's body, such as the thoracic cavity, pleural cavity, gallbladder and liver, renal pelvis, bladder, etc. In this case, it can be used not only in feeding medicine solutions, etc., to the prescribed area in the human body, but also in removing body fluids from the prescribed area in the body. Also, in Embodiment 4, ring-shaped member (78) is used and movable gripped parts (72), (73) are urged into main body (71). However, one may also adopt a scheme in which, instead of ring-shaped member (78), the interior of the housing is used as the pressing means. Similarly, one may also make use of the ring-shaped member as the pressing means in Embodiments 1-3.

In addition, various materials can be used in manufacturing the previously described indwelling needle. For example, external needle (10), the portion other than metal needle (21) of internal needle (20), needle tip protective part (30), etc., can be made of polypropylene, polycarbonate, polyurethane, nylon, silicone, polyether imides, polyether ether ketones, ABS resins, polyethylene, and other materials. Also, cannula (11) may be made of fluororesins, polyurethane, and other materials. In addition, the shapes and materials for forming indwelling needle, etc., appropriate modifications can be made within the technical range of the present disclosure.

What is claimed is:

1. An indwelling needle assembly comprising:
   an outer cannula having a proximal end, a distal end and a housing attached to the proximal end, the housing defining an interior space which decreases in diameter towards the proximal end;
   an inner needle having a sharpened distal tip portion and a proximal end secured to a hub; and
   a needle tip protector positioned within the interior space of the housing and slidably positioned about the inner needle, the needle tip protector having a first end defining a first through-hole of a first diameter and a second end defining a second through-hole of a second diameter smaller than the first diameter; and
   at least one inwardly movable blocking member supported on the needle tip protector, wherein the inner needle includes an enlarged diameter adjacent the distal tip portion which is larger than the first diameter but smaller than the second diameter;
   wherein withdrawing the inner needle from the outer cannula in a proximal direction causes the enlarged diameter of the inner needle to engage the needle tip protector adjacent the second through-hole to effect withdrawal of the needle tip protector from the housing, wherein withdrawal of the needle tip protector from the housing causes the at least one blocking member to move inwardly to block the distal tip portion of the inner needle.

2. The indwelling needle assembly according to claim 1, wherein the at least one blocking member includes at least two blocking members.

3. The indwelling needle assembly according to claim 1, wherein the at least one blocking member includes two blocking members diametrically opposed to one another.

4. The indwelling needle assembly according to claim 2, wherein the blocking members are attached to the needle tip protector at a proximal end of the blocking members.

5. The indwelling needle assembly according to claim 4, wherein the blocking members have distal ends formed to provide a locking action when mutually engaged.

6. The indwelling needle assembly according to claim 3, wherein the needle tip protector further comprises a slip ring arranged such that upon withdrawal of the inner needle from the outer cannula, the slip ring is caused to slide over the blocking members to move the blocking members inwardly.

7. The indwelling needle assembly according to claim 6, wherein the blocking members are attached to the needle tip protector at a proximal end of the blocking members.

8. The indwelling needle assembly according to claim 7, wherein the blocking members have distal ends formed to provide a locking action when mutually engaged.

9. The indwelling needle according to claim 2, wherein the blocking members are attached to the needle tip protector at a distal end of the blocking members.

10. The indwelling needle assembly according to claim 9, wherein two of the blocking members have proximal ends forming a tongue and groove interrelation.

* * * * *